United States Patent
Schara et al.

(10) Patent No.: US 10,251,532 B2
(45) Date of Patent: Apr. 9, 2019

(54) METHOD AND SYSTEM FOR USING A VARIABLE DIRECTION OF VIEW ENDOSCOPE WITH A ROBOTIC ENDOSCOPE HOLDER

(75) Inventors: Nathan Jon Schara, Pasadena, CA (US); Eric Lawrence Hale, Altadena, CA (US); Hans David Hoeg, Arcadia, CA (US)

(73) Assignee: Karl Storz Imaging, Inc., Goleta, CA (US)

(*) Notice: Subject to any disclaimer, the term of this patent is extended or adjusted under 35 U.S.C. 154(b) by 3545 days.

(21) Appl. No.: 11/083,277

(22) Filed: Mar. 17, 2005

(65) Prior Publication Data

US 2005/0256371 A1 Nov. 17, 2005

Related U.S. Application Data

(60) Provisional application No. 60/554,973, filed on Mar. 20, 2004.

(51) Int. Cl.
| | | |
|---|---|---|
| *A61B 1/00* | (2006.01) | |
| *A61B 1/313* | (2006.01) | |
| *A61B 90/50* | (2016.01) | |
| *A61B 90/00* | (2016.01) | |
| *A61B 34/30* | (2016.01) | |

(52) U.S. Cl.
CPC .......... *A61B 1/00149* (2013.01); *A61B 1/313* (2013.01); *A61B 90/50* (2016.02); *A61B 34/30* (2016.02); *A61B 90/361* (2016.02)

(58) Field of Classification Search
CPC .................. A61B 1/00149; A61B 1/00183
USPC .................. 600/102, 103, 117, 173, 174
See application file for complete search history.

(56) References Cited

U.S. PATENT DOCUMENTS

| | | | | | |
|---|---|---|---|---|---|
| 3,994,557 | A | * | 11/1976 | Hopkins | 359/374 |
| 4,517,963 | A | * | 5/1985 | Michel | 600/126 |
| 5,351,676 | A | * | 10/1994 | Putman | 600/117 |
| 5,432,543 | A | * | 7/1995 | Hasegawa et al. | 348/45 |
| 5,524,180 | A | * | 6/1996 | Wang et al. | 600/118 |
| 6,024,695 | A | * | 2/2000 | Taylor et al. | 600/102 |
| 6,120,433 | A | * | 9/2000 | Mizuno et al. | 600/102 |
| 6,191,809 | B1 | * | 2/2001 | Hori et al. | 348/45 |
| 6,314,211 | B1 | * | 11/2001 | Kim et al. | 382/285 |
| 6,668,185 | B2 | * | 12/2003 | Toida | 600/425 |
| 6,695,774 | B2 | * | 2/2004 | Hale et al. | 600/173 |
| 2004/0138524 | A1 | * | 7/2004 | Ueda et al. | 600/102 |

\* cited by examiner

*Primary Examiner* — Alexandra L Newton
*Assistant Examiner* — Rynae Boler
(74) *Attorney, Agent, or Firm* — Whitmyer IP Group LLC

(57) ABSTRACT

A system and method for using a variable direction of view endoscope in conjunction with an electromechanical endoscope holder.

12 Claims, 3 Drawing Sheets

METHOD AND SYSTEM FOR USING A VARIABLE DIRECTION OF VIEW ENDOSCOPE WITH A ROBOTIC ENDOSCOPE HOLDER

CROSS-REFERENCE TO RELATED APPLICATIONS

This application claims the benefit of U.S. provisional application Ser. No. 60/554,973 filed on Mar. 20, 2004, entitled "Method and system for using a variable direction of view endoscope with a robotic endoscope holder", the contents of which are incorporated herein by reference.

FIELD OF THE INVENTION

The present invention relates to electromechanical positioning of variable direction of view endoscopes.

BACKGROUND OF THE INVENTION

Computer-controlled electromechanical positioning systems for endoscopes are disclosed in U.S. Pat. No. 5,515,478 to Wang and U.S. Pat. No. 5,524,180 to Wang et al. These multi degree-of-freedom devices provide the operator with the ability to accurately control the endoscopic viewing direction through electronic switches or voice commands and have become an important part of robotic minimally invasive surgical procedures. The shortcoming of such endoscopic positioning systems is that they can only provide a limited endoscopic viewing range because the mechanical mobility is outside rather than inside the inspection site and because these positioning systems are designed for use with fixed-angle endoscopes which do not have a variable line of sight. This is especially true in neuroendoscopy, sinoscopy, or otoscopy, where the endoscope shaft is physically constrained or must remain largely stationary to avoid injuring the patient.

Variable direction of view endoscopes, as exemplified in U.S. Pat. No. 3,856,000 to Chikama, U.S. Pat. No. 6,371,909 to Hoeg, U.S. Pat. No. 6,560,013 to Ramsbottom, U.S. Pat. No. 4,697,577 to Forkner, U.S. Pat. No. 6,500,115 to Krattiger et al., U.S. Pat. No. 5,762,603 to Thompson, U.S. Pat. No. 5,313,306 to Kuban, U.S. Pat. No. 5,800,341 to McKenna et al., U.S. Pat. No. 6,364,830 to Durell, U.S. Pat. No. 3,572,325 to Bazell et al., U.S. Pat. No. 3,880,148 to Kanehira, U.S. Pat. No. 5,257,618 to Kondo, and by LTF TYPE V3 Laparo-Thoraco Videoendoscope from Olympus Optical Co., can vary their line of sight at the tip of the instrument, thus transferring the viewing mobility to the tip and relieving the problem of limited viewing range. Hale et al. discloses a computer-controlled variable direction of view endoscope, affording the operator accurate viewing navigation and positioning capabilities even from a fixed view point.

A heretofore unanticipated combination of a computer-controlled endoscope positioning system and a computer-controlled variable direction of view endoscope affords new and powerful navigation capabilities. For example, coupling the 7DOF robotic endoscope holder disclosed in U.S. Pat. No. 5,524,180 to Wang with the 3DOF computer-controlled endoscope of U.S. Pat. No. 6,663,559 to Hale et al., yields a new 7DOF system with significant dexterity and wide ranging navigation capabilities. Many moves previously possible only in virtual endoscopy, which uses a virtual camera to "fly" through 3D volumetric models constructed from data obtained with a noninvasive imaging technique (MRI, CT, PET, ultrasound) are thus possible with a real camera having real-time optical imaging. Specifically, such a combined system would enable i) accurate scanning behind surfaces, ii) precise lesion or tumor inspection from nearly all angles, iii) precise post-operative diagnoses, iv) more versatility in approaching surgical targets, v) locking to a specific view and keeping it steady while the mechanism changes configuration, vi) stereoscopic reconstructions, and vii) better stereotactic navigation.

Accordingly, the primary object of the present invention is to provide a system which merges/combines the advantages of robotic endoscope holders with the advantages of a variable direction of view endoscope and provides additional advantages. Still further objects and advantages will become apparent from the ensuing description and drawings.

BRIEF SUMMARY OF THE INVENTION

In accordance with the present invention, a variable direction of view endoscope is coupled to robotic endoscope holder.

In some embodiments, the invention comprises a method for allowing a user to remotely control a movement of a variable direction of view endoscope having a longitudinal axis, a tip, and a view vector movable relative to the longitudinal axis, the method comprising the steps: a) establishing an original position of the tip of the endoscope; b) inputting a command provided by a user to move the endoscope in a desired direction relative to an object displayed on a display device; c) computing an incremental movement of the endoscope based on the command provided by the user and on the original position of the endoscope; d) moving the endoscope in the desired direction so that the tip of the endoscope always moves in a direction commanded by the user; e) inputting a command provided by the user to move the view vector relative to the longitudinal axis in a desired direction relative to an object displayed on the display device; and f) moving the view vector relative to the longitudinal axis so that the view vector moves in a direction commanded by the user.

In some cases, the step of inputting a command comprises a save command. In certain cases, the step of inputting a command comprises a return command.

In other embodiments, the invention comprises a system that allows a user to remotely control a movement of a variable direction of view endoscope and its view vector, wherein the view vector is movable relative to the longitudinal axis of the endoscope, and wherein the endoscope has a tip and is coupled to a display device that displays an object, comprising: a) movement means for moving the endoscope, the movement means having an original position; b) input means for inputting a command provided by the user to move the endoscope in a desired direction relative to the object displayed by the display device; and c) control means for receiving the command to move the endoscope in the desired direction, computing an incremental movement of the movement means based on the command and the original position of the movement means so that the surgical instrument tip moves in the desired direction, and providing output signals to the movement means to move the movement means the incremental movement so that the surgical instrument tip always moves in the desired direction commanded by the user; d) input means for inputting a command provided by the user to move the view vector in a desired direction relative to the object displayed by the display device; e) control means for receiving the command to move the view vector and moving the view vector in the desired direction; and f) movement means for moving the view vector.

In other embodiments, the invention comprises a system for allowing a surgeon to control a variable direction of view endoscope with a longitudinal axis and a view vector which is movable relative to the longitudinal axis, and wherein the endoscope is inserted through an incision of a patient with the incision defining a pivot point, the system comprising: a) an articulate arm having an end effector for holding the endoscope, and an actuator for moving the end effector, the articulate arm further having a passive joint located between the end effector and the actuator, the articulate arm for pivoting the endoscope about the pivot point; b) a input device for receiving input commands from the surgeon; and c) a controller for receiving the input commands, for computing movements of the articulate arm and the view vector based on the input commands, and for providing output commands to actuate the active joint and for moving the endoscope about the pivot point and for moving the view vector relative to the endoscope longitudinal axis.

DETAILED DESCRIPTION OF THE INVENTION

The following detailed description illustrates the invention by way of example, not by way of limitation of the principles of the invention. This description will enable one skilled in the art to make and use the invention, and describes several embodiments, adaptations, variations, alternatives and uses of the invention, including what we presently believe is the best mode of carrying out the invention.

Preferred Embodiment

Figure 1:
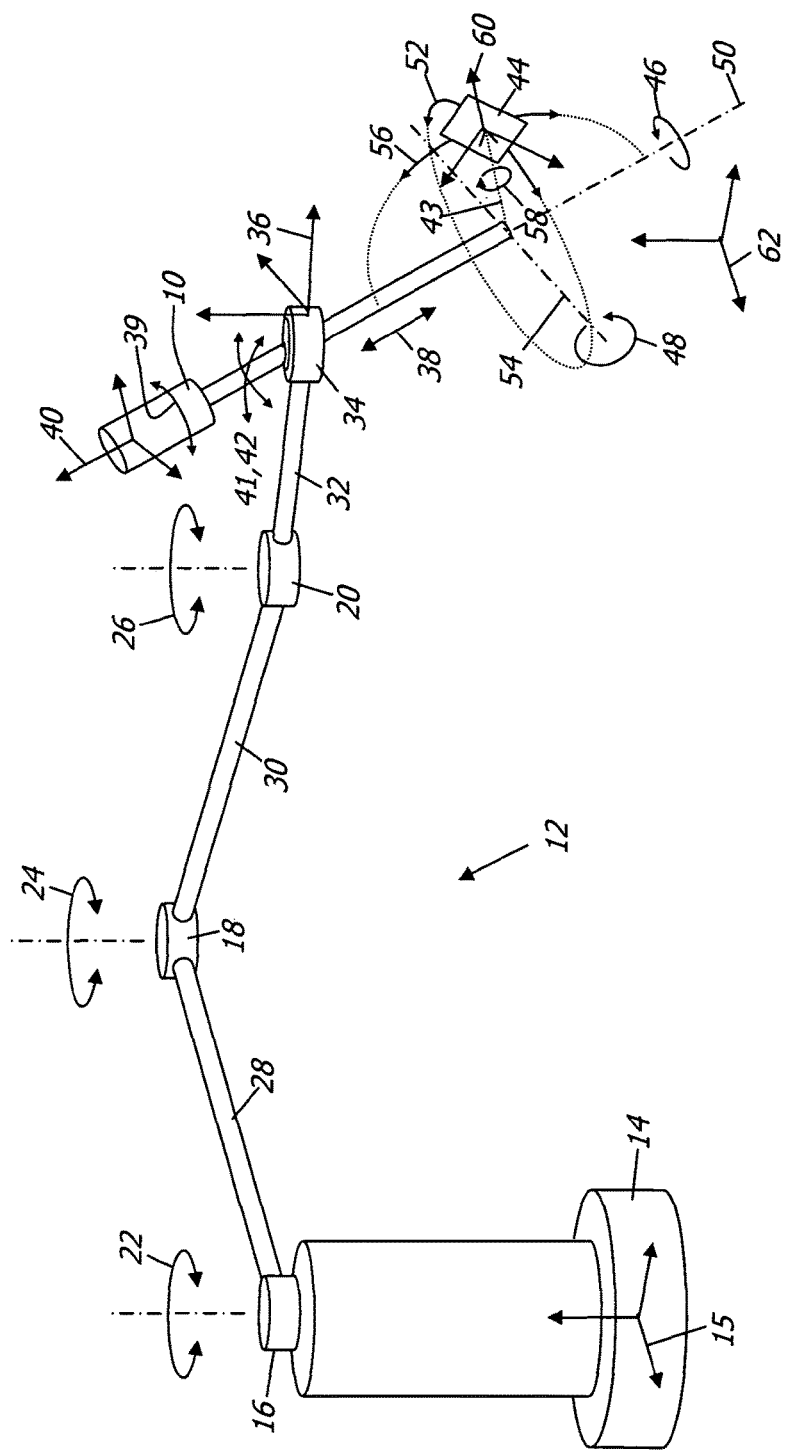
FIG. 1 shows variable direction of view endoscopes coupled to a robotic endoscope holder according to the preferred embodiment of the present invention.

Referring now to the drawings, in which like reference numbers represent similar or identical structures throughout, FIG. 1 is a diagram of a basic variable direction of view endoscope 10 held by a robotic arm 12 with a base 14 and a base frame 15. The robotic arm 12 has three actuated revolute joints 16, 18, 20 with rotational degrees of freedom 22, 24, 26. The joints 16, 18, 20 are connected by links 28, 30. A third link 32 extends from the joint 20 to an end-effector 34 which has a prismatic joint (not explicitly shown) and an associated tool frame 36. The dynamic spatial relationship between the tool frame 36 and the base frame 15 is determined by the geometry of the joints 16, 18, 20 and links 28, 30, 32 and is in robotics called the forward kinematic transformation (or conversely the inverse kinematic transformation). Aside from the ability to slide and rotate the endoscope 10 along a linear degree of freedom 38 and a rotational degree of freedom 39, the end-effector 34 passively holds the scope 10 and senses the dynamic attitude of an endoscope frame 40 fixed to the endoscope 10. A mapping between the endoscope frame 40 and the tool frame 36 is given in U.S. Pat. Nos. 5,515,478 and 5,524,180 to Wang et al. and incorporates two additional degrees of freedom 41, 42 which allow the endoscope 10 to passively tilt relative to the end-effector 34. The endoscope 10 itself has a view vector 43 and an associated view field 44 with at least two degrees of freedom 46, 48. The $1^{st}$ degree of freedom 46 permits rotation of the view vector 43 about the endoscope longitudinal axis 50, which allows the view vector 43 to scan in a latitudinal direction 52. This degree of freedom 46 is a duplicate of the rotational degree of freedom 39; only one of these is necessary for the full-fledged operation of the present invention. The $2^{nd}$ degree of freedom 48 permits rotation of the view vector 43 about an axis 54 perpendicular to the longitudinal axis 50, which allows the view vector 43 to scan in a longitudinal direction 56. A $3^{rd}$ degree of freedom 58 may also be available because it is usually possible to adjust the rotational orientation of the endoscopic image. A view frame 60 is associated with the view field 44. The mapping between the view frame 60 and the endoscope frame 40 is described in U.S. Pat. No. 6,663,559 to Hale et al. who also describe the use of an environment frame or an arbitrary user-defined frame 62 dictating the motion of the view vector 43. An overall kinematic relationship between the view frame 60 (or the arbitrary frame 62) and the base frame 15 can thus be calculated, providing the operator with 10 (one redundant) overall degrees of freedom for controlling the position, direction, and orientation of the endoscopic view point. This integrated system is thus a physical version of a virtual endoscopy method allowing the user to fly through an endoscopic space.

Figure 2:
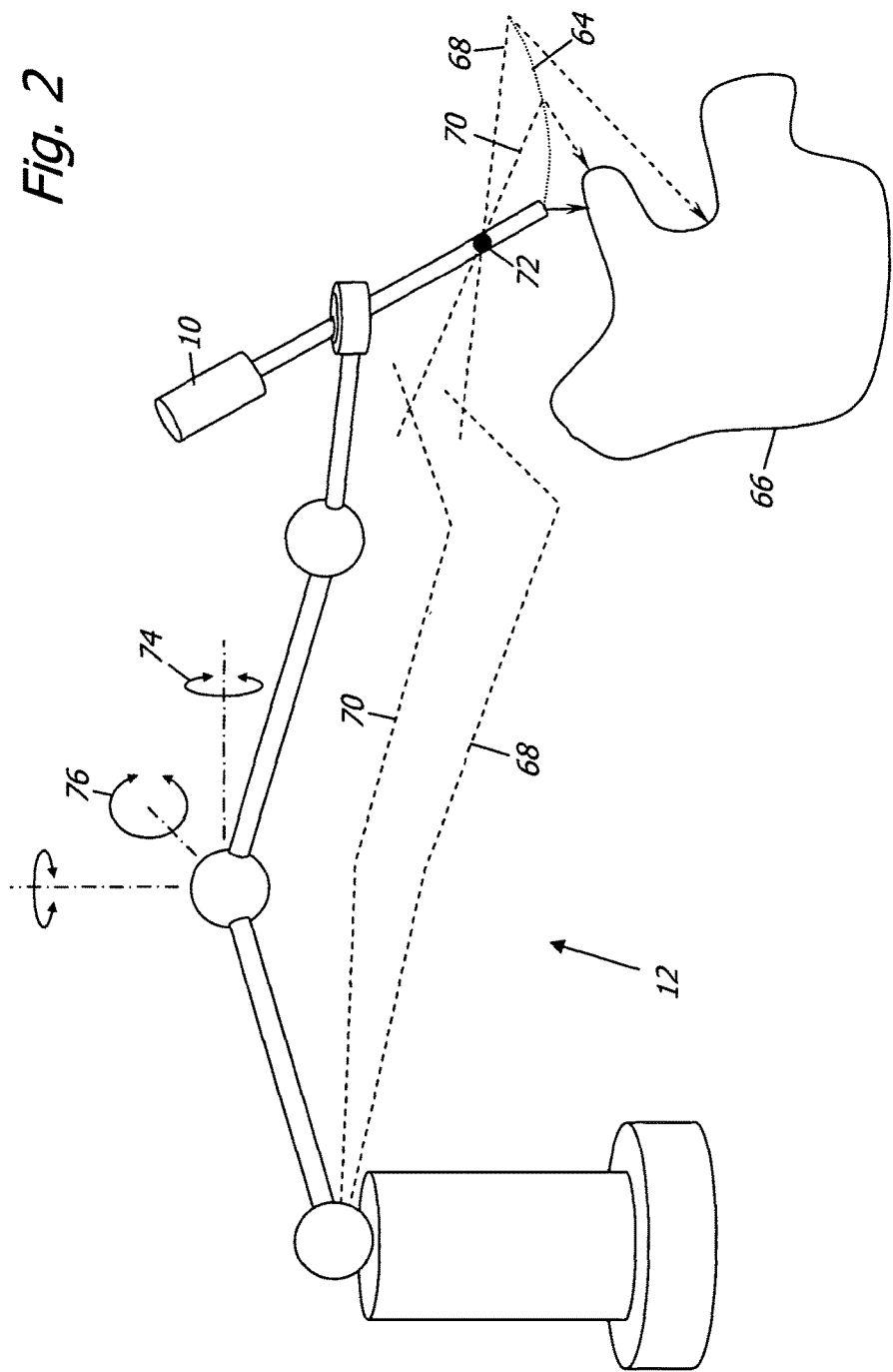
FIG. 2 illustrates the concept of scanning the lateral surface of an organ according to the preferred embodiment of the present invention.

FIG. 2 illustrates the concept of moving the tip of the endoscope 10 through a trajectory 64 associated with inspecting the far side of an organ 66. The view vector 43 scans the surface as the endoscope 10 moves through the endoscopic space. Certain previous configurations 68, 70 of the integrated arm-endoscope system are shown. The endoscopic entry point 72 into the patient (not shown) acts as a fulcrum which applies lateral forces as the robotic arm 12 is actuated. Because the endoscope 10 is passively supported by the end-effector 34, these lateral forces cause the endoscope 10 to tilt without the risk of injuring the patient. Note that the robotic arm 12 shown in this case has universal joints rather than revolute, yielding two additional degrees of freedom 74, 76 for each joint for a system total of 16. Depending on the application any type of joint or link can be used.

Figure 3:
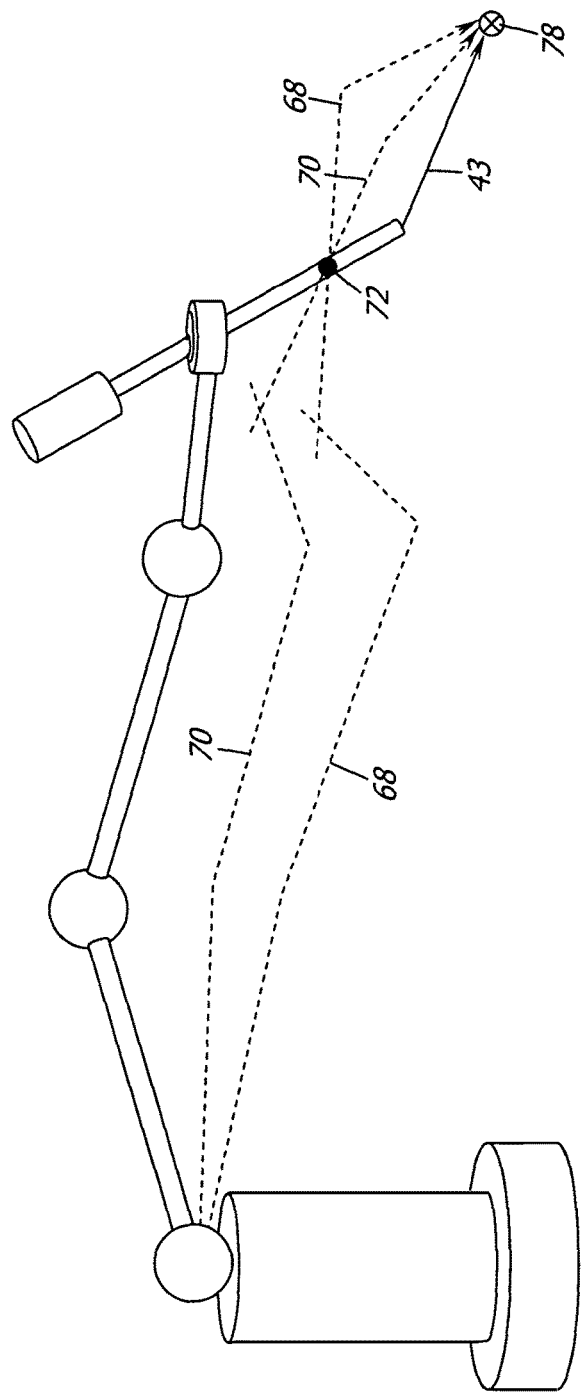
FIG. 3 shows the principle of visually locking on an object while changing the position of the endoscope to accommodate surgical tools or obtain stereoscopic data.

FIG. 3 shows how the system of the present invention can be used to keep the view vector 43 trained on a target 74 while the system configuration changes. This technique is useful because it can provide topographic information which is difficult to obtain with a single 2D endoscopic view. Further, being able to view the same object from many different angles makes it possible to obtain stereoscopic still images of the object and perform general 3D endoscopic photography.

Accordingly, the present invention provides an integrated system for robotically controlling a variable direction of view endoscope, merging the advantages of electromechanical endoscope positioning and variable direction of view endoscopy and affording new capabilities such as 3D endoscopic photography.

The present invention has been described above in terms of a presently preferred embodiment so that an understanding of the present invention can be conveyed. However, there are many alternative modes of operation not specifically described herein but with which the present invention is applicable. For example, although specific manipulators where described, any mechanism known from the field of robotics would fall under the scope of this invention. Also, many different types of variable direction of view endoscopes such as rigid scopes with deflectable tips, flexible scopes, or semiflexible scopes, can be used. Different mathematical parameterizations would be required in order to accommodate the specific kinematics associated with various scopes, but the governing principle as described in this invention would remain the same. In addition, while the examples were given with respect to endoscopes for use in surgical procedures, the present invention would be equally applicable with respect to borescopes or the like for use in non-medical situations. The scope of the present invention should therefore not be limited by the embodiments illustrated, but rather it should be understood that the present invention has wide applicability with respect to robotic control of variable direction endoscopic viewing instruments. All modifications, variations, or equivalent elements and implementations that are within the scope of the appended claims should therefore be considered within the scope of the invention.

We claim:

1. A method for performing 3D endoscopic photography using a variable direction of view endoscope having a longitudinal axis, a tip, and a view vector movable relative to the longitudinal axis, the method comprising the steps:
   a) securing the endoscope on an articulate arm comprising at least three universal joints and an end-effector that passively holds the endoscope while the articulate arm is actuated;
   b) establishing an original position of the tip of the endoscope;
   c) inputting an endoscope moving command provided by a user to move the endoscope in a desired direction relative to an object displayed on a display device;
   d) computing an incremental movement of the endoscope based on the command provided by the user and on the original position of the endoscope;
   e) moving the endoscope in the desired direction so that the tip of the endoscope always moves in a direction commanded by the user and so that the endoscope changes its angle about a fulcrum;
   f) inputting a view vector moving command provided by the user to move the view vector relative to the longitudinal axis in a desired direction relative to an object displayed on the display device;
   g) moving the view vector relative to the longitudinal axis of the distal end of the endoscope so that the view vector moves in a direction commanded by the user so that the view of the object is changed;
   h) repeating steps c), d), e), f), and g) to obtain a plurality of views of the object; and
   i) using the plurality of views to obtain at least one stereoscopic image of the object.

2. The method of claim 1, wherein the step of a) securing further comprises that the end-effector comprises a prismatic joint.

3. The method of claim 1, wherein the articulate arm of step of a) further comprises at least three segments connected by the universal joints.

4. A method for performing 3D endoscopic photography using a variable direction of view endoscope having a longitudinal axis, a tip, and a view vector movable relative to the longitudinal axis, the method comprising the steps: a) securing the endoscope on an articulate arm comprising at least three segments, a plurality of joints, and an end-effector that passively holds the endoscope; b) establishing an original position of the tip of the endoscope; c) inputting a command to change a view of an object provided by the endoscope and displayed on a display device; d) computing an incremental movement of the articulate arm and the view vector based on the command and on the original position of the endoscope; e) moving the endoscope according to the computed incremental movement by moving of at least one of the plurality of joints and by causing the endoscope to change its angle about a fulcrum; and f) moving the view vector relative to the longitudinal axis of the distal end of the endoscope according to the computed incremental movement so that the view of the object is changed; g) repeating steps c), d), e), and f) to obtain a plurality of views of the object; and h) using the plurality of views to obtain at least one stereoscopic image of the object.

5. The method of claim 4, wherein at least one of the plurality of joints is a universal joint.

6. The method of claim 4, wherein the step of a) securing further comprises that the end-effector comprises a prismatic joint.

7. The method of claim 4, wherein the step of a) securing further comprises that the end-effector comprises at least one sensor that senses the attitude of the endoscope.

8. The method of claim 4, wherein the step of e) moving the endoscope further comprises that the fulcrum comprises an entry-point into a patient's body.

9. The method of claim 1, wherein the step of a) securing further comprises that the end-effector comprises at least one sensor that senses the attitude of the endoscope.

10. The method of claim 1, wherein the step of e) moving the endoscope further comprises that the fulcrum comprises an entry-point into a patient's body.

11. The method of claim 1, wherein robotic control of the variable direction of view endoscope is integrated with electromechanical positioning of the endoscope.

12. The method of claim 1, wherein the method is performed during a surgical procedure.

* * * * *